(12) United States Patent
Chang et al.

(10) Patent No.: US 6,517,520 B2
(45) Date of Patent: Feb. 11, 2003

(54) PERIPHERALLY INSERTED CATHETER WITH FLUSHABLE GUIDE-TUBE

(75) Inventors: Joseph J. Chang, Irving, TX (US); Anja Metzger, Stillwater, MN (US)

(73) Assignee: Ethicon Endo Surgery, Inc., Cincinnati, OH (US)

( * ) Notice: Subject to any disclaimer, the term of this patent is extended or adjusted under 35 U.S.C. 154(b) by 22 days.

(21) Appl. No.: 09/746,258

(22) Filed: Dec. 21, 2000

(65) Prior Publication Data

US 2002/0082559 A1 Jun. 27, 2002

(51) Int. Cl.[7] ............................................. A61M 5/178
(52) U.S. Cl. .................. 604/164.11; 604/246; 604/264; 604/524; 604/533
(58) Field of Search .................. 604/164.01, 164.1, 604/164.11, 246, 264, 523, 524, 525, 527, 533, 537, 164.09

(56) References Cited

U.S. PATENT DOCUMENTS

| 4,239,042 A | 12/1980 | Asai |
| 4,850,975 A | 7/1989 | Furukawa |
| 5,357,961 A | 10/1994 | Fields et al. |
| 5,391,152 A | 2/1995 | Patterson |
| 5,951,495 A * | 9/1999 | Berg et al. .................. 600/435 |
| 6,398,773 B1 * | 6/2002 | Bagaoisan et al. ..... 604/101.04 |

FOREIGN PATENT DOCUMENTS

EP 0347170 12/1989

OTHER PUBLICATIONS

HV Technologies, Medical Product Manufacturing News Hotline, "Thin–Wall Polyimide Composite Tubing Systems Developed", Jan./Feb. 1995, 1 page, Trenton, Georgia.

* cited by examiner

Primary Examiner—Noah P. Kamen
(74) Attorney, Agent, or Firm—Blakely, Sokoloff, Taylor & Zafman, LLP

(57) ABSTRACT

Methods and apparatuses for inserting a catheter into a patient.

In one exemplary embodiment, a guide-tube is disposed within the catheter lumen to guide the insertion of the catheter into a patient. The catheter having two ends and at least a catheter lumen and is surrounded by a catheter wall. The guide-tube is hollow, and having a guide-tube lumen which is surrounded by a guide-tube wall. The dimension of the guide-tube is less than that of the catheter lumen.

15 Claims, 6 Drawing Sheets

PERIPHERALLY INSERTED CATHETER WITH FLUSHABLE GUIDE-TUBE

BACKGROUND OF THE INVENTION

This invention relates to the field of medical devices, especially a catheter assembly.

A peripherally inserted catheter (PIC) is used for accessing a vascular system. PIC is a device used for a long term and repeated access to a patient's vascular system for it avoids multiple injections and thus, minimizes trauma and pain to the patient. A PIC is often short and tends to move, at least slightly, into and out of the body leading to infections and frequent replacements.

Peripherally inserted central catheters (PICC) were designed to solve problems associated with PIC. A PICC is a much longer catheter and it is designed to be inserted percutaneously (through the skin) such that it reaches deep into the vascular system. A PICC is typically used to reach the superior vena cava of the heart to deliver treatment drugs. An example of a catheter reaching to the heart is shown in FIG. 1.

A PICC must be soft, pliable and bendable. In placing a PICC in the heart, one must be able to maneuver the PICC through tortuous venous paths and natural blockages. To facilitate in the inserting of a PICC into a patient, techniques for stiffening the catheter for insertion have been developed, such as a guidewire. A guidewire can be inserted within the catheter for stiffness during insertion and removed when insertion is successfully achieved.

One example of a guidewire for PICC insertion is described in U.S. Pat. No. 5,357,961. In this method, a guidewire wrapped with coiled spring is inserted within a PICC. This method also contemplates a way to flush the PICC before, during, and after the insertion of the PICC into a patient so as to make such insertion of the PICC and the removal of the guidewire from the PICC easier and smoother.

Problems associated with such a guidewire include the fact that the guidewire is wrapped with a coiled spring. A coiled spring tends to damage the interior of a catheter. While a coiled spring may damage the interior of the catheter, it is needed in the prior art nevertheless, because according to the prior art, the coiled spring gives the guidewire shape and contour to facilitate the process of a PICC insertion.

Another problem associated with a guidewire of the prior art is that in order to ease the insertion of a PICC into a patient, flushing the catheter with fluid is necessary. Leakage is to ease one problem associated with flushing. U.S. Pat. No. 5,357,961 employed a three-way connector with one port dedicated to fluid injection to prevent leakage. However, a three-way connector is bulky and inconvenient.

SUMMARY OF THE INVENTION

To solve the problems associated with a guidewire of the prior art, the present invention provides apparatuses and methods for a flushable guide-tube to be used, in one exemplary embodiment, with a PICC.

In one exemplary embodiment, an apparatus of the present invention includes a catheter having two ends and a catheter and at least a lumen, which is surrounded by a catheter wall. A guide-tube is disposed within the catheter lumen to guide the insertion of the catheter into a patient. The guide-tube is hollow, and having at least a guide-tube lumen which is surrounded by a guide-tube wall. The dimension of the guide-tube is less than that of the catheter lumen.

In another exemplary embodiment, the method of inserting a catheter into a patient includes providing a catheter having two catheter ends and at least a catheter lumen, which is surrounded by a catheter wall. Inserting a hollow guide-tube into the catheter; the guide-tube further having two guide-tube ends, at least a guide-tube lumen which is surrounded by a guide-tube wall, and having a dimension which is less than a dimension of the catheter lumen. Disposing a first connector over the catheter. Disposing a second connector over the guide-tube. Disposing the guide-tube inside the catheter by coupling the second connector to the first connector. Attaching a syringe filled with a solution to the guide-tube. Threading the catheter having the guide-tube inserted therein into a patient. Flushing the guide-tube with the solution as necessary to achieve threading. Disconnecting the second connector from the first connector and withdrawing the guide-tube from the catheter when threading is achieved. Attaching a fluid drip line to the first connector as necessary.

BRIEF DESCRIPTION OF THE DRAWINGS

FIG. 1A illustrates an example of a conventional guidewire 100 of a prior art.

FIGS. 2-1, 2-2 and 2-3 illustrate examples of three different designs of a coiled spring guidewire of a prior art.

FIG. 3 illustrates a catheter assembly according to one exemplary embodiment of the present invention.

FIG. 3A illustrates an example of how a guide-tube according to the present invention may be made.

DETAILED DESCRIPTION OF THE INVENTION

Figure 1:
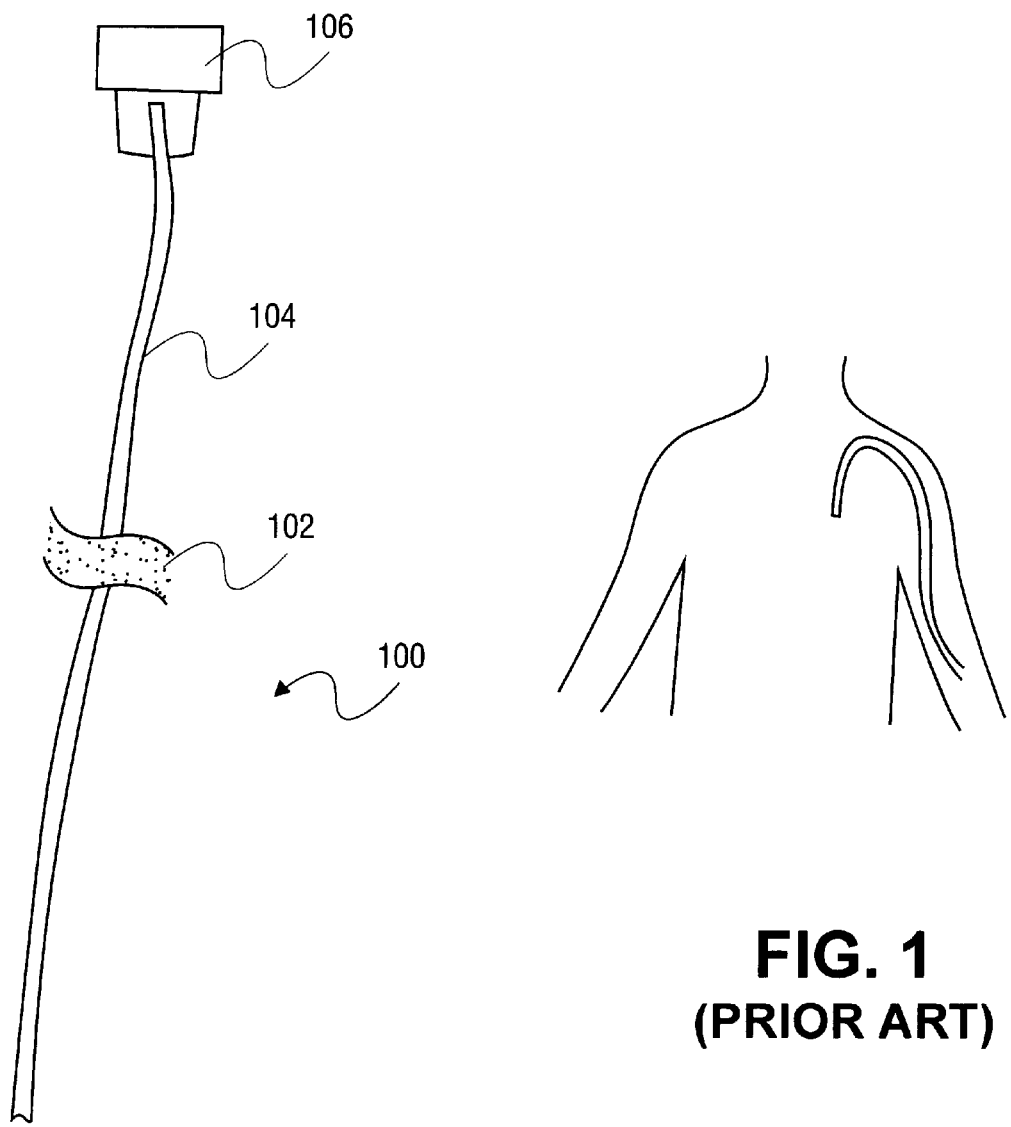
FIG. 1 illustrates an example of a prior art in which a PICC is inserted into a patient's heart.

The reference characters refer to the same parts throughout different views of the invention unless indicated otherwise.

FIG. 1A illustrates an example of a conventional guidewire 100 of a prior art. In this example, guidewire 100 is a solid rod 104 being coupled to a connector 106. A connector 106 is typically a solid plug. A conventional guidewire such as that shown in FIG. 1A is wrapped with wire to give what is called a coiled spring guidewire.

Figure 2:
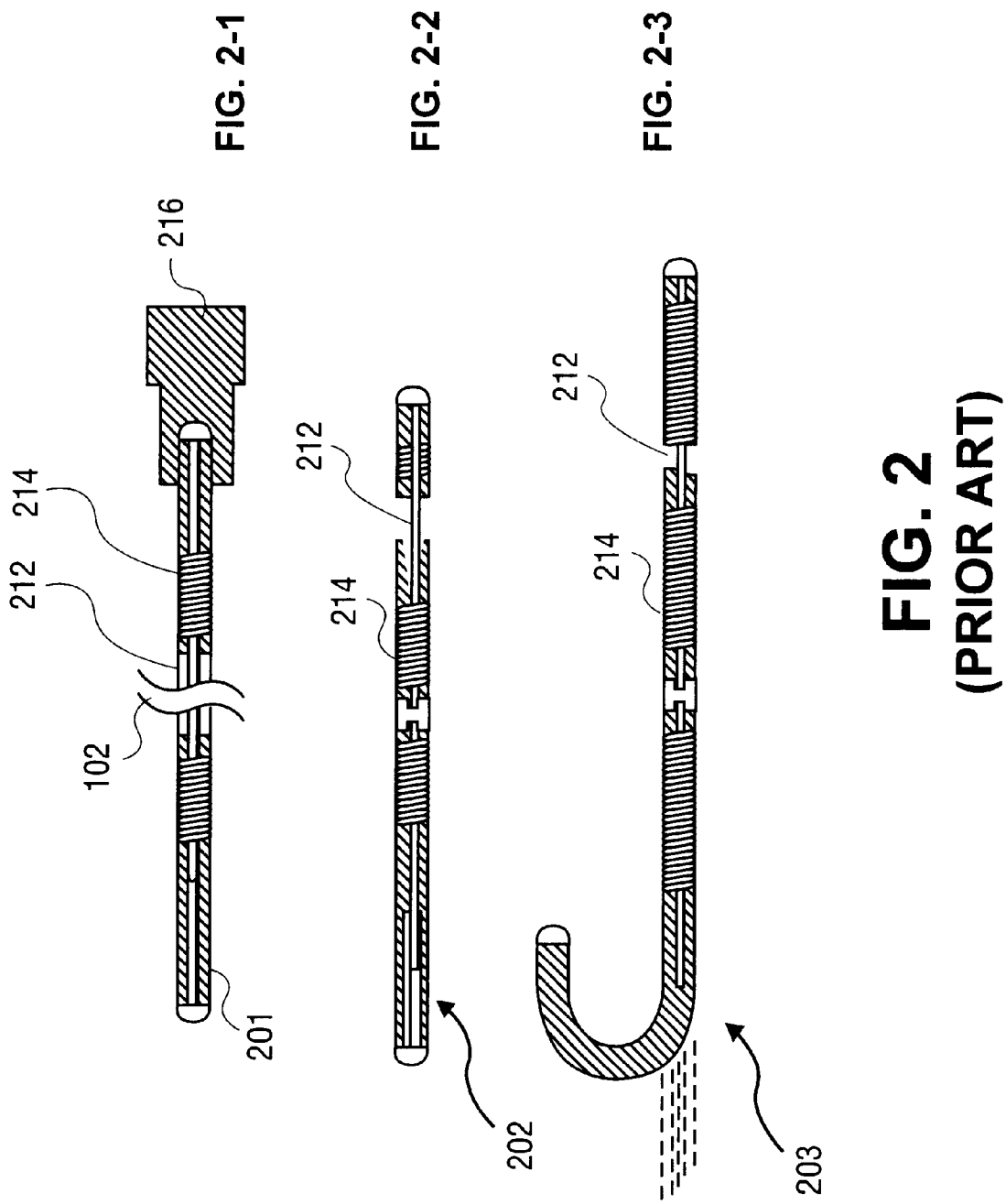
Figures 3, 3A:
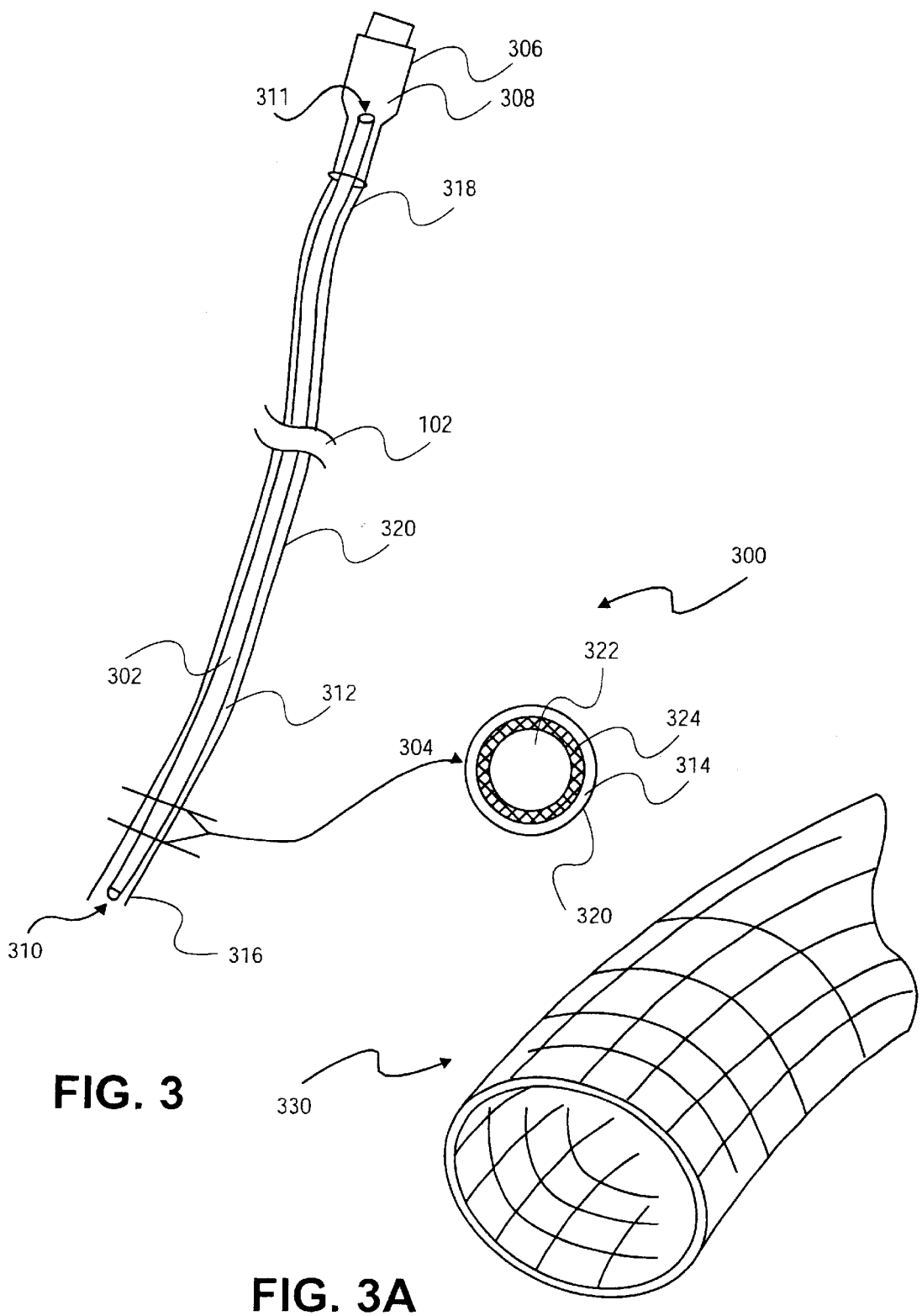

FIGS. 2-1, 2-2, and 2-3 illustrate three different designs of a conventional coiled spring guidewire. FIG. 2-1 shows a straight tip coiled spring guidewire 201, FIG. 2-2 shows a moveable coiled spring guidewire 202, and FIG. 2-3 shows a moveable J-tip coiled spring guidewire 203. As depicted in all three figures, coiled spring guidewire 201, 202, and 203 are all made out of an outer coiled spring 214 wrapping around a solid central core rod 212. Coiled spring guidewire 201, 202 or 203 can be connected to a solid plug 216 to hold it in place inside a catheter (not shown).

In contrary to the conventional guidewire, the present invention discloses embodiments of a guide-tube for use with a catheter or a PICC. The word "catheter" used in following description refers to both an all purpose catheter as well as a PICC.

In a preferred embodiment, catheter assembly 300 comprising a guide-tube 302 which is inserted or disposed within catheter 312. (See FIG. 3).

The placement of a catheter 312 within a vein, artery or other internal area of a patient requires catheter 312 to be maneuvered through tortuous paths. Guide-tube 302 that has a smaller outer diameter than the internal diameter of the catheter 312 may be initially inserted into the catheter and then, catheter 312 equipped with guide-tube 302 may be inserted into a patient. One of the purpose for using guide-tube 302 is to provide added rigidity or stiffness to the catheter during the insertion procedure since catheters are generally made of a very pliable material to permit them to follow the natural internal paths through veins, arteries and other paths.

One advantage for using guide-tube 302 to guide the insertion of catheter 312 as opposed to the conventional guidewire 100 is that guide-tube 302 has a smooth surface. A conventional guidewire typically has a spring coiled or twisted braided on the outer surface of a solid rod. (See FIGS. 2-1, 2-2 and 2-3). In such conventional technology, the removal of the guidewire from the catheter may damage the interior surface of the catheter.

Further, more resistance may be present during the removal of a coiled spring or a twisted braided guidewire from the catheter than the removal of a smooth surface guide-tube according to the present invention. Resistance built up during removal of a coiled spring or a twisted braided guidewire means that extra fluid flushing of the catheter is necessary. On the other hand, the removal of guide-tube 302 according to this invention may not require flushing catheter 312 during removal.

Furthermore, due to its smoothness, guide-tube 302 may be cut or trimmed to a desirable length without fraying.

Catheter 312 may be an elongated catheter, for example having a length of thirty centimeters (30 cm). Catheter 312 is typically used for intravenous medication, injection chemotherapy, antibiotic treatment, or chemical environment monitoring. Catheter 312 is often flexible and typically made out of a biocompatible material that is pliable and soft, such as, a medical grade polyurethane, silastic, silicone rubber or a similar material. Catheter 312 may further include two catheter ends, 316 and 318, and at least a catheter lumen 314 which is surrounded by a catheter wall 320 and extending longitudinally along the body of catheter 312. (See FIG. 3). Catheter 312 may have multiple lumens to serve a particular purpose.

In one embodiment, as FIG. 3 illustrated, a catheter assembly 300 includes a catheter 312 having a guide-tube 302 disposed within the catheter lumen 314 to guide the insertion of catheter 312 into a patient. Guide-tube 302 is a hollow tube, and having a guide-tube lumen 322 which is surrounded by a guide-tube wall 324.

Guide-tube 302 may have a dimension that is less than that of catheter lumen 314. For example, when a catheter has one lumen such as lumen 314, and has an outer diameter of 0.070", its inner diameter is about 0.055". Here, the outer diameter of a guide-tube such as guide-tube 302 should be about 0.045" for a snug fitting between the guide-tube and the catheter. When guide-tube 302 is snuggly inserted or disposed within catheter 312, maneuvering catheter assembly 300 into a patient's body is easier and interference into catheter assembly 300 is minimized.

Guide-tube 302 may have a length that is substantially equal to or less than the length of catheter 312. In such instance, no trimming of guide-tube would be necessary.

In one embodiment, guide-tube 302 is a stainless steel braided tube 330 as shown in FIG. 3A. A thin-wall tubing system technology developed by HV Technologies, Inc., Trenton, Ga. may be employed to manufacture stainless steel braided tube 330 for guide-tube 302. With HV Technologies, guide-tube 302 may be made out of a variety of materials, for examples, plastics or metal. Alternatively, guide-tube 302 may be a metal reinforced tube made out of a variety of materials. (See Medical Product Manufacturing News, January/February 1995, "Thin-Wall Polyimide Composite Tubing Systems Developed").

In one embodiment, guide-tube 302 is a hollow tube that is a metal reinforced micro tube. Preferably, guide-tube 302 has a dimension that is smaller than the dimension of catheter 312. Cross-section 304 depicts the insertion of guide-tube 302 inside catheter 312 and that guide-tube 302 is smaller than catheter lumen 314.

Guide-tube 302 can be made out of any biocompatible material that is flexible and yet stiff enough to provide rigidity to catheter 312 during insertion. Guide-tube 302 may be made out of a material that has a shape memory property. Such a guide-tube 302 may be bent to a desired shape during the insertion of catheter assembly 300 and unbent to return guide-tube 302 to the original shape during the removal of catheter assembly 300 due to its inherent shape memory property.

Alternatively, guide-tube 302 may be manufactured into a predetermined shape for use with a particular purpose. For instance, guide-tube 302 may be manufactured like a J shape hollow tube. In this example, guide-tube 302 will be at least equivalent to J tip guidewire depicted in FIG. 2.

Figure 4:
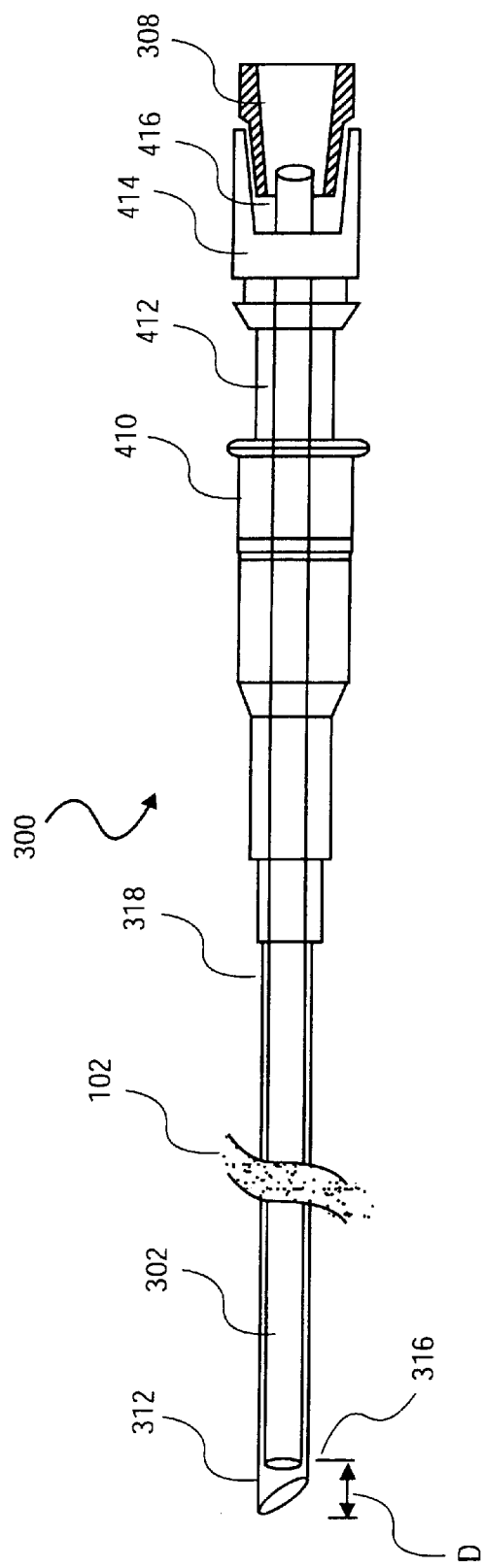
FIG. 4 illustrates a catheter assembly according to one exemplary embodiment of the present invention.

FIG. 4 illustrates yet another embodiment. In this embodiment, catheter assembly 300 comprises catheter 312, guide-tube 302, connector 410, outlet port 412, and connector 414.

Catheter 312 is an elongated body having a catheter lumen 314 and two guide-tube ends, 310 and 311 (See FIG. 3). Guide-tube 302, also having ends 310 and 311, is disposed within catheter 314 of catheter 312. Once guide-tube 302 is inserted or disposed inside catheter lumen 314, guide-tube end 310 and catheter end 316 are the ends being inserted into a patient's body through point of entry 102.

Catheter end 318 may be disposed inside a first connector, connector 410. Connector 410 is hollow. Connector 410 may be a female hub, which is fastened to catheter 312 via end 318. When connector 410 and catheter 312 are fastened together, a continuous and leakless assembly is thus established. Connector 410 may slide over to connect to a hollow outlet port 412. Connector 410 is selected such that it fits snugly over outlet port 412 to create a good seal. Further, connector 410 will not slide off without some substantial force.

Guide-tube end 311 is securely coupled to a second connector, connector 308, which is hollow and which may be a luer connection or a female hub connector. Guide-tube 302 coupling to connector 308 may be disposed through outlet port 412 and into catheter 312. Connector 308 and outlet port 412, being hollow, enable fluid to be injected therethrough and into guide-tube 302. Connector 308 is also selected such that it fits snugly into outlet port 412 to provide a good seal. Outlet port 412 is selected such that it has a dimension large enough to allow guide-tube 302 to be disposed therethrough.

Connector 308 may act as a handle for guide-tube 302. Connector 308 would have a larger gripping surface than would guide-tube 302. It is thus, easier to handle and manipulate catheter assembly 300 with connector 308. Further, because connector 308 is just a standard hub connector or a luer connector, no new device needs to be made and no modification for catheter dressing is necessary.

Outlet port 412 may also be connected to a hollow third connector, connector 414, which can be a hub connector having insertion port 416. In that event, guide-tube 302 coupling to connector 308 may be disposed through third connector 413, via insertion port 416, and into catheter 312.

As illustrated in FIG. 4, when completely inserted, guide-tube 302, having a total length that is shorter than catheter 312, may be fixed securely at connector 308 such that there is some distance D from catheter 312 tip to guide-tube 302 tip. Distance D is preferably 0.5 cm. Distance D provides additional protection for a patient's vein because guide-tube 302 would within catheter 302, hence, chances of puncture or irritation to the vein of the patient are minimized.

Figure 4A:
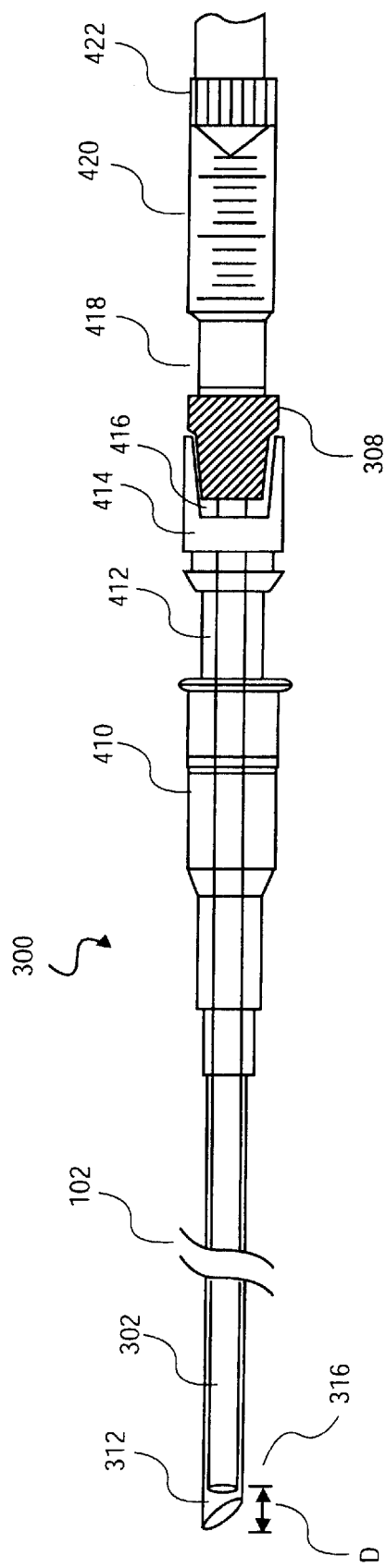
FIG. 4A illustrates a catheter assembly according to one exemplary embodiment of the present invention in which a syringe is coupled to the assembly.

FIG. 4A illustrates yet, another embodiment of catheter assembly 300. In this example, catheter assembly 300 comprises catheter 312, guide-tube 302, connector 410, outlet port 412, connector 414, connector 418 and syringe 420.

In one embodiment, syringe 420 is coupled to connector 418. Syringe 420 may be a typical injecting syringe used for injecting fluid or medication into a patient and is available commercially. Connector 418 may be a hub connector that may be disposed into connector 308. Connector 418 is selected such that it would fit snugly into connector 308 to provide a good seal for fluid injection. Since connector 308 couples directly to guide-tube 302, syringe 420 would be connected to guide-tube 302 and not catheter 312.

Syringe 420 may be used to inject treatment fluid or medication into guide-tube 302 during the insertion of catheter assembly 300 into a patient. In one embodiment, a fluid may be injected into catheter assembly 300 when guide-tube 302 is still inserted within catheter 312. Injecting fluid through guide-tube 302 is one way of flushing of guide-tube 302.

A solution such as saline having some heparin may be used to fill syringe 420, which is then used for flushing guide-tube 302. Heparin concentration may be in the range of 10 units/cc to 100 units/cc of heparin in saline. Flushing of guide-tube 302 may occur simultaneously with the threading or inserting of catheter assembly 300.

Flushing of guide-tube 302 is necessary when one meets a resistance or an obstruction inside the patient's body during insertion of catheter assembly 300. For instance, when catheter 312 equipped with guide-tube 302 is being threaded through a path in patient's body, catheter 312 may meet resistance in this path. Fluid injection may push this path open so as to allow the threading to continue to destination.

A novel feature between guide-tube 302 according to this invention and a conventional guidewire is that guide-tube 302 is flushable while a guidewire is not flushable. One reason is that since guide-tube 302 is hollow, fluids can be flushed through guide-tube 302 and since a conventional guidewire is a solid rod, no fluid can be flushed through. Any flushing done with a conventional guidewire will be through the void area between the guidewire and the catheter, (i.e., flushing is only done through the catheter and outside the guidewire). On the other hand, flushing according to exemplary embodiments of this invention may be achieved through guide-tube 302 and not through catheter 312.

Flushing directly through guide-tube 302 ensures that there will be no leaking problem into catheter assembly 300. Another advantage according to examples of this invention is that since flushing according to this invention is accomplished through flushing guide-tube 302, catheter 312 is remained uninterfered. Thus, medication to be injected into the patient is not interfered or diluted by other flushing solutions.

Catheter assembly 300 may come pre-assembled. Guide-tube 302 may already be inserted or disposed catheter 312. One advantage for this is that it prevents guide-tube 302 from moving too quickly through a patient's vein thus, minimizing discomfort or irritation. Further, there is less of a chance that an operator will puncture catheter 312 inside the patient's vein during insertion of guide-tube 302 into catheter 312. Undetected puncture of catheter wall 320 of catheter 312 once it is inside the patient will lead to complications such as insufficient medication delivery or misdirection of such deliver.

Figure 5:
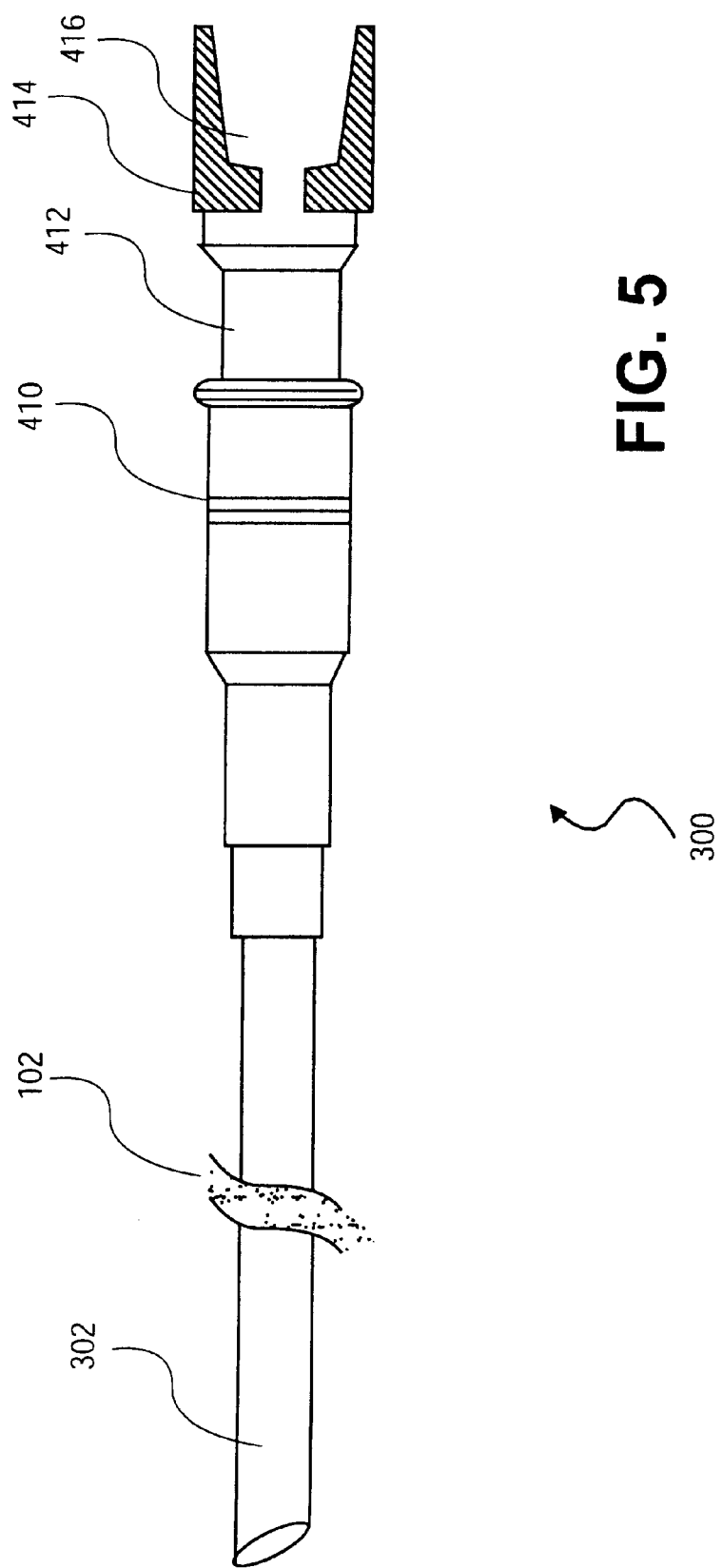
FIG. 5 illustrates a catheter assembly according to one exemplary embodiment of the present invention in which the guide-tube is removed from the catheter assembly.

FIG. 5 illustrates another embodiment of catheter assembly 300. In this example, catheter assembly 300 comprises catheter 312, connector 410, outlet port 412, and connector 414. FIG. 5 illustrates that after successful insertion of catheter 312 into a patient's body, guide-tube 302 and syringe 420 of FIG. 4A have been removed. Catheter 312 can be taped in place in the skin of the patient. An I.V. drip line or an infusion syringe (not shown) may be inserted into connector 414 and medication can be injected into a patient.

One exemplary method of inserting a PICC in a patient is depicted in FIG. 4A. An operator fills syringe 420 with a flushing solution such as saline containing heparin. The operator then connects syringe 420 to guide-tube 302 that is already inserted within catheter 312 as discussed in the embodiments above.

The operator flushes guide-tube 302 by depressing on plunger 422 of syringe 420 thus, injecting flushing solution into guide-tube 302. Flushing guide-tube 302 prior to inserting catheter assembly 300 into a patient allows the operator to check for any product defects, such as leakage in guide-tube wall or catheter wall or blockage in catheter assembly 300. Defects or leakages would mean the operator will need to repeat the puncture in the patient leading to unnecessary discomfort or pain. The operator will know that catheter assembly 300 is ready for use when drops of solution emerges from the catheter 312 tip and not anywhere else along the body of catheter 312.

When guide-tube 302 is already inserted within catheter 312 as supplied by a manufacturer, no trimming by the operator is necessary since guide-tube may be manufactured to be about the same length or shorter than catheter 312. In event when trimming is nevertheless required, excess guide-tube may be withdrawn and excised through connector 308.

The operator then begins inserting catheter assembly 300 at a point of entry 102 on a patient's body. A Peelable PICC introducer known by those skilled in the art may be used to facilitate the insertion of catheter 312 into patient (Johnson and Johson Catalog No. 97913. (Not depicted in figures).

As mentioned above, flushing guide-tube 302 may be necessary to facilitate smooth insertion. In that event, the operator flushes guide-tube 302 as above. Flushing would reduce resistance to allow catheter 312 to continue on its path in the patient's body or veins. Flushing may also prevent any blood or blood clothing that accumulates inside guide-tube 302 to facilitate insertion.

Once catheter 312 is successful inserted, the operator removes guide-tube 302 from catheter assembly 300. The operator may first disconnect connector 308 from catheter assembly 300. Then, using connector 308 as a handle the operator withdraws guide-tube 302 from catheter 312. During the removal of guide-tube 302 from catheter 312, the operator may also flush guide-tube 302 to prevent fluid from the patient to be withdrawn. Lastly, the operator may withdraw introducer needle 600 from the patient.

Guide-tube 302 may also be coated with a thin layer of a conventional lubricant or hydrophilic polymer coating, such as a hydrogel, polyethylene oxide, polyvinyl porylidone, pluronic, hydrophilic polyurethane or hydroxy ethyl methacholate. This coating may provides lubrication and may facilitate the insertion and removal of guide-tube 302 from catheter assembly 300. Also, back pressure that may occur during the removal of guide-tube 302 may be prevented by continuous flushing of guide-tube 302 during the removal.

Once guide-tube 302 is removed from catheter assembly 300, the operator then connects another syringe to the assembly for the injection of treatment fluid or medication (not illustrated).

We claim:

1. A catheter assembly comprising:
   a catheter having two catheter ends and at least a catheter lumen which is surrounded by a catheter wall of said catheter; and
   a guide-tube disposed within said catheter lumen, said guide-tube to guide said catheter into a patient, said guide-tube being hollow, having a dimension which is less than a dimension of said catheter lumen, and further including two guide-tube ends, a guide-tube lumen which is surrounded by a guide-tube wall of said guide-tube;
   a first connector coupled to a proximal end of said catheter; and
   a second connector coupled to a proximal end of said guide-tube, said second connector to receive a fluid injection apparatus and to be disposed within said first connector.

2. A catheter assembly as in claim 1 wherein said guide-tube has a length that is substantially equal to said catheter such that no trimming is necessary.

3. A catheter assembly comprising:
   a catheter having two catheter ends and at least a catheter lumen which is surrounded by a catheter wall of said catheter;
   a guide-tube disposed within said catheter lumen, said guide-tube to guide said catheter into a patient, said guide-tube being hollow, having a dimension which is less than a dimension of said catheter lumen, and further including two guide-tube ends, a guide-tube lumen which is surrounded by a guide-tube wall of said guide-tube;
   a first connector, said first connector to dispose over said catheter;
   a second connector, said second connector being hollow and having two connecting ends, one of said two connecting ends couples to one of said two guide-tube ends and disposes within said first connector; and
   a syringe, said syringe couples to said second connector at the remaining end of said two connecting ends.

4. A catheter assembly as in claim 3 wherein said guide-tube is a metal reinforced tube.

5. A catheter assembly as in claim 3 wherein said guide-tube is a metal tube.

6. A catheter assembly as in claim 3 wherein said guide-tube is coated with a hydrophilic polymer coating.

7. A method of assembling a catheter comprising:
   providing a catheter, said catheter having two catheter ends and a catheter lumen which is surrounded by a catheter wall of said catheter; and
   inserting a guide-tube into said catheter, said guide-tube disposed within said catheter lumen, said guide-tube to guide said catheter into a patient and having two guide-tube ends, a guide-tube lumen which is surrounded by a guide-tube wall of said guide-tube, and having a dimension which is less than a dimension of said catheter lumen;
   attaching a first connector to a proximal end of said catheter; and
   disposing a second connector within said first connector, said second connector in communication with said guide-tube lumen and configured to receive a syringe.

8. A method of assembling a catheter comprising:
   providing a catheter, said catheter having two catheter ends and a catheter lumen which is surrounded by a catheter wall of said catheter;
   inserting a guide-tube into said catheter, said guide-tube disposed within said catheter lumen, said guide-tube to guide said catheter into a patient and having two guide-tube ends, a guide-tube lumen which is surrounded by a guide-tube wall of said guide-tube, and having a dimension which is less than a dimension of said catheter lumen;
   disposing a first connector over said catheter;
   disposing a second connector within said first connector, said second connector being hollow and having two connecting ends;
   coupling said second connector to one of said two guide-tube ends at one of said two connecting ends; and
   coupling a syringe to the other of said two connecting ends.

9. A method of assembling a catheter as in claim 8 wherein said guide-tube is a metal reinforced tube.

10. A method of assembling a catheter in claim 9 wherein said guide-tube is a metal tube.

11. A method of assembling a catheter in claim 9 wherein said guide-tube is coated with a hydrophilic polymer coating.

12. A method of inserting a catheter comprising:
   providing a catheter, said catheter having two catheter ends and a catheter lumen which is surrounded by a catheter wall of said catheter;
   disposing a guide-tube into said catheter lumen of said catheter, said guide-tube to guide said catheter into a patient, said guide-tube having two guide-tube ends, a guide-tube lumen which is surrounded by a guide-tube wall of said guide-tube, and having a dimension which is less than a dimension of said catheter lumen;
   disposing a first connector over said catheter, said first connector is configured to accept a second connector, said second connector being hollow and having two connecting ends;
   coupling said connector to one of said two guide-tube ends at one of said two connecting ends;
   filling a syringe with a solution;
   coupling said syringe to the other of said two connecting ends of said second connector;
   threading said catheter having said guide-tube inserted therein into a patient;

flushing said guide-tube with said solution as necessary to achieve said threading; and withdrawing said second connector and said guide-tube from said catheter when said threading is achieved.

13. A method of inserting a catheter as claim 12 wherein said flushing of said guide-tube occurs simultaneously with said threading such that said flushing to help ease said inserting of said catheter past an obstruction in said patient.

14. A method of inserting a peripherally inserted central catheter comprising:

providing a catheter, said catheter having two catheter ends and a catheter lumen which is surrounded by a catheter wall of said catheter;

disposing a guide-tube into said catheter lumen of said catheter, said guide-tube to guide said catheter into a patient, said guide-tube having two guide-tube ends, a guide-tube lumen which is surrounded by a guide-tube wall of said guide-tube, and having a dimension which is less than a dimension of said catheter lumen;

disposing a first connector over said catheter, said first connector is configured to accept a second connector, said second connector being hollow and having two connecting ends;

coupling said connector to one of said two guide-tube ends at one of said two connecting ends;

filling a syringe with a solution;

coupling said syringe to the other of said two connecting ends of said second connector;

threading said catheter having said guide-tube inserted therein into a patient;

flushing said guide-tube with said solution as necessary to achieve said threading; and withdrawing said second connector and said guide-tube from said catheter when said threading is achieved.

15. A method of inserting a catheter as claim 14 wherein said flushing of said guide-tube occurs simultaneously with said threading such that said flushing to help ease said inserting of said catheter past an obstruction in said patient.

* * * * *